United States Patent
Metz et al.

(10) Patent No.: US 6,834,840 B1
(45) Date of Patent: Dec. 28, 2004

(54) MEDICAL DEVICE SUPPORT ASSEMBLY

(75) Inventors: Darrell L. Metz, Batesville, IN (US); Kenneth Merkel, Batesville, IN (US); Matthew Visca, Fairfield, OH (US); Roger Hildwein, Woodinville, WA (US); Jack E. Smith, Dayton, OH (US)

(73) Assignee: Hill-Rom Services, Inc., Wilmington, DE (US)

( * ) Notice: Subject to any disclaimer, the term of this patent is extended or adjusted under 35 U.S.C. 154(b) by 190 days.

(21) Appl. No.: 09/629,524

(22) Filed: Aug. 1, 2000

(51) Int. Cl.[7] .............................................. F16M 11/00

(52) U.S. Cl. .................. 248/410; 248/161; 248/297.51; 403/377

(58) Field of Search ................................ 248/410, 161, 248/286.1, 285.1, 287.1, 297.51; 403/377, 379.1, 379.2, 379.5

(56) References Cited

U.S. PATENT DOCUMENTS

| | | |
|---|---|---|
| 383,815 A | 5/1888 | Kilborn |
| 1,290,809 A | 1/1919 | Truax |
| 1,490,650 A | 4/1924 | Wagner |
| 1,674,081 A * | 6/1928 | Adams |
| 1,919,114 A | 7/1933 | Ley |
| 2,470,524 A | 5/1949 | Scudder |
| 2,673,771 A | 3/1954 | Krewson |
| 2,696,963 A | 12/1954 | Shepherd |
| RE24,290 E * | 3/1957 | MacKnight |
| 2,943,831 A * | 7/1960 | Goss .......................... 248/495 |
| 3,004,743 A | 10/1961 | Wenger |
| 3,402,947 A * | 9/1968 | Lewis |
| 3,552,577 A | 1/1971 | Latham, Jr. |
| 3,588,023 A * | 6/1971 | Cohen |
| 3,674,294 A | 7/1972 | Kirkham |
| 3,814,023 A | 6/1974 | Stantial |
| 4,005,844 A | 2/1977 | Richmond |
| 4,113,222 A | 9/1978 | Frinzel |
| 4,163,536 A * | 8/1979 | Heller et al. |
| 4,190,224 A | 2/1980 | LeBlanc et al. |
| 4,225,104 A | 9/1980 | Larson |
| 4,262,872 A | 4/1981 | Kodet |
| D260,816 S | 9/1981 | Zissimopoulos et al. |
| 4,339,104 A | 7/1982 | Weidman |
| 4,511,157 A | 4/1985 | Wilt, Jr. |
| 4,511,158 A | 4/1985 | Varga et al. |
| 4,559,036 A | 12/1985 | Wunsch |
| 4,600,209 A | 7/1986 | Kerr, Jr. |
| 4,616,797 A | 10/1986 | Cramer |
| 4,629,074 A * | 12/1986 | Toder |
| D289,604 S | 5/1987 | Gallant et al. |
| 4,691,397 A | 9/1987 | Netzer |
| 4,702,448 A | 10/1987 | LoJacono et al. |
| 4,718,892 A | 1/1988 | Yung-Ho |
| 4,729,576 A | 3/1988 | Roach |
| 4,744,536 A | 5/1988 | Bancalari |
| 4,905,882 A | 3/1990 | Ross |
| 4,905,944 A | 3/1990 | Jost et al. |
| 4,925,444 A | 5/1990 | Orkin et al. |
| 4,945,592 A | 8/1990 | Sims et al. |
| 4,966,340 A | 10/1990 | Hunter |
| 4,969,768 A | 11/1990 | Young |
| 4,997,150 A | 3/1991 | Mardollo |

(List continued on next page.)

FOREIGN PATENT DOCUMENTS

DE 29903222 6/1999

OTHER PUBLICATIONS

Color photographs (Figs. 1–7) of I.V. Pole.

Primary Examiner—Korie Chan
(74) Attorney, Agent, or Firm—Bose McKinney & Evans LLP (57) ABSTRACT

A medical device support assembly is provided including a base pole, an adjustment pole, and a coupling configured to couple the adjustment pole to the base pole.

11 Claims, 5 Drawing Sheets

U.S. PATENT DOCUMENTS

| | | | |
|---|---|---|---|
| 5,000,124 A | * 3/1991 | Bergen | 119/63 |
| 5,016,307 A | 5/1991 | Rebar | |
| 5,078,349 A | 1/1992 | Smith | |
| 5,083,807 A | 1/1992 | Bobb et al. | |
| 5,094,418 A | 3/1992 | McBarnes, Jr. et al. | |
| 5,108,066 A | 4/1992 | Lundstrom | |
| 5,110,076 A | 5/1992 | Snyder et al. | |
| 5,112,019 A | 5/1992 | Metzler et al. | |
| 5,125,607 A | 6/1992 | Pryor | |
| 5,174,533 A | 12/1992 | Pryor et al. | |
| 5,207,642 A | 5/1993 | Orkin et al. | |
| 5,224,681 A | * 7/1993 | Lundstrom | |
| 5,319,816 A | 6/1994 | Ruehl | |
| 5,322,253 A | 6/1994 | Stevens | |
| 5,400,995 A | 3/1995 | Boyd | |
| 5,407,163 A | 4/1995 | Kramer et al. | |
| 5,588,166 A | 12/1996 | Burnett | |
| 5,636,823 A | 6/1997 | Boyd | |
| 5,647,491 A | 7/1997 | Foster et al. | |
| 5,657,884 A | 8/1997 | Zilincar, III | |
| 5,699,988 A | 12/1997 | Boettger et al. | |
| 5,704,577 A | 1/1998 | Gordon | |
| 5,772,162 A | * 6/1998 | Lin | |
| 5,820,086 A | 10/1998 | Hoftman et al. | |
| 5,826,847 A | 10/1998 | Warner et al. | |
| 5,857,685 A | 1/1999 | Phillips et al. | |
| 5,888,014 A | * 3/1999 | Lung et al. | |
| 6,224,027 B1 | * 5/2001 | Johnson et al. | |

* cited by examiner

MEDICAL DEVICE SUPPORT ASSEMBLY

BACKGROUND AND SUMMARY OF THE INVENTION

The present invention relates to IV poles configured to support medical devices. More specifically the present invention relates to IV poles having adjustable lengths and a mechanism for fixing the length.

During the administration of medical care, it is often necessary to position a medical device near a patient. It is convenient to support the medical device away from the patient so that the patient can rest or move about without interfering with the medical device. IV poles are often used to support these medical devices in a position away from the patient. Such IV poles may be free standing, attached to a bed, attached to a wheelchair, or attached to any other support. Because patients and/or medical devices vary in their size and/or configuration, it is often convenient to adjust the overall length of the IV pole for a given situation.

According to the present disclosure, an IV pole assembly is provided that is configured to support a medical device. The assembly includes a base pole, an adjustment pole, and a coupling configured to couple the adjustment pole to the base pole. The adjustment pole is configured to support the medical device. The base pole and the adjustment pole cooperate to define a pole assembly length. The adjustment pole is configured to move in a first direction relative to the base pole to decrease the pole assembly length and in a second direction relative to the base pole to increase the pole assembly length. The coupling includes a lock member configured to lock the position of the adjustment pole relative to the base pole. The coupling further includes a release that is configured to move the lock member between a first position blocking movement of the adjustment pole in the first direction and permitting movement of the adjustment pole in the second direction and a second position permitting movement of the adjustment pole in the first and second directions.

According to another embodiment of the present disclosure, an IV pole assembly is provided that is configured to support a medical device thereon. The assembly includes a base pole, an adjustment pole configured to support the medical device, and a substantially flat lock member. The lock member couples the adjustment pole to the base pole. The lock member is moveable between a first position that permits movement of the adjustment pole relative to the base pole and a second position locking the position of the adjustment pole relative to the base pole.

According to yet another embodiment of the present disclosure, an IV pole assembly is provided that is configured to support a medical device. The assembly includes a base pole, an adjustment pole configured to support the medical device, and a coupling. The adjustment pole has a longitudinal axis and the coupling is configured to couple the adjustment pole to the base pole. The coupling includes a lock member configured to move between first and second positions. The lock member, when in the first position, and the longitudinal axis define a first angle therebetween. The lock member, when in the second position, and the longitudinal axis of the adjustment pole define a second angle therebetween that deviates from the first angle. The lock member is configured to permit movement of the adjustment pole relative to the base pole with the lock member in the first position. The lock member is configured to block movement of the adjustment pole relative to the base pole with the lock member in the second position.

Additional features of the disclosure will become apparent to those skilled in the art upon consideration of the following detailed description when taken in conjunction with the accompanying drawings.

DETAILED DESCRIPTION OF THE DRAWINGS

Figure 1:
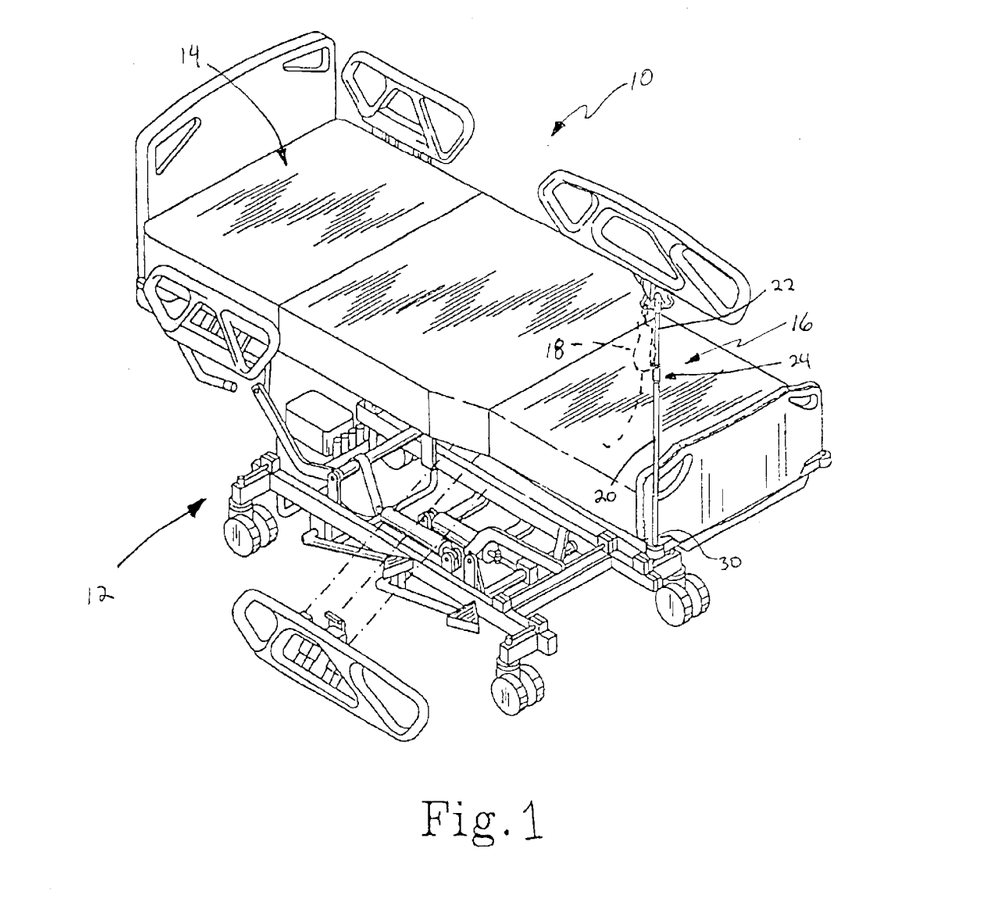
FIG. 1 is a perspective view of a hospital bed and an IV pole assembly coupled to the hospital bed.

As shown in FIG. 1, a hospital bed 10 is provided having a bedframe 12, a medical device support and a mattress 14 positioned over bedframe 12, and an IV pole or medical device support assembly 16 coupled to bedframe 12. IV pole assembly 16 is configured to support an IV bag 18 (shown in phantom), IV pump, monitor or any other medical device near a patient during treatment or recovery of the patient so that the patient can rest or move about without interfering with the medical device. Because patients and/or medical devices vary in their size and/or configuration, it is often convenient to adjust the overall length of IV pole assembly 16 for a given situation. According to the present disclosure, IV pole assembly 16 is removable from bed 10 so that a caregiver may couple it to a wheelchair, walker, another bed, or any other patient support. According to alternative embodiments, the IV pole assembly is provided on a base as a free-standing unit.

Figure 2:
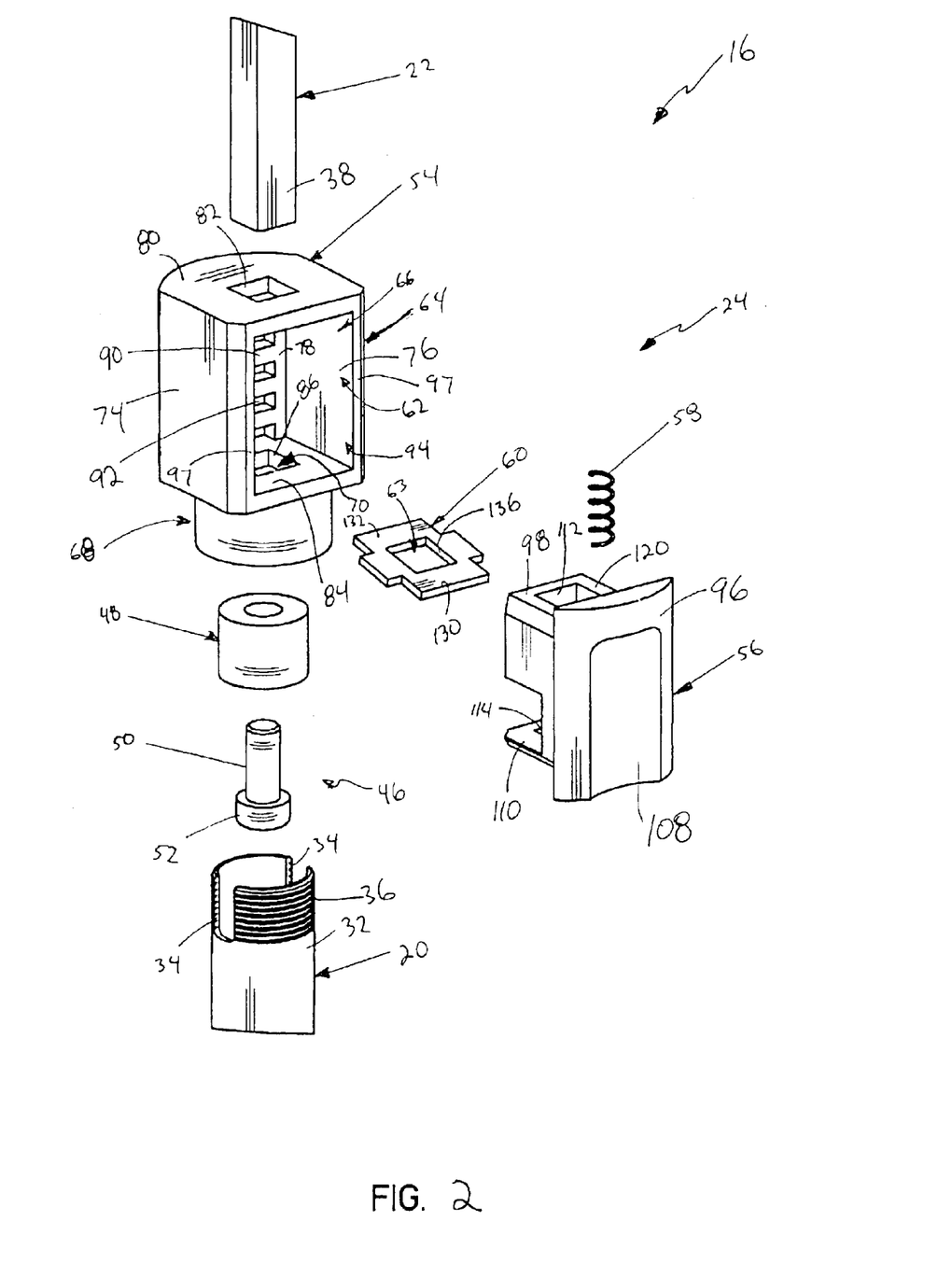
FIG. 2 is an exploded perspective view of the IV pole assembly of FIG. 1, with portions broken away, showing the IV pole assembly including a lower tube-shaped base pole, a box-like housing positioned over the base pole, a bolt and washer positioned between the housing and the base pole, a square rod-shaped adjustment pole positioned over the housing, a release, a plate-like lock member positioned between the release and the housing, and a spring.
Figures 3, 6:
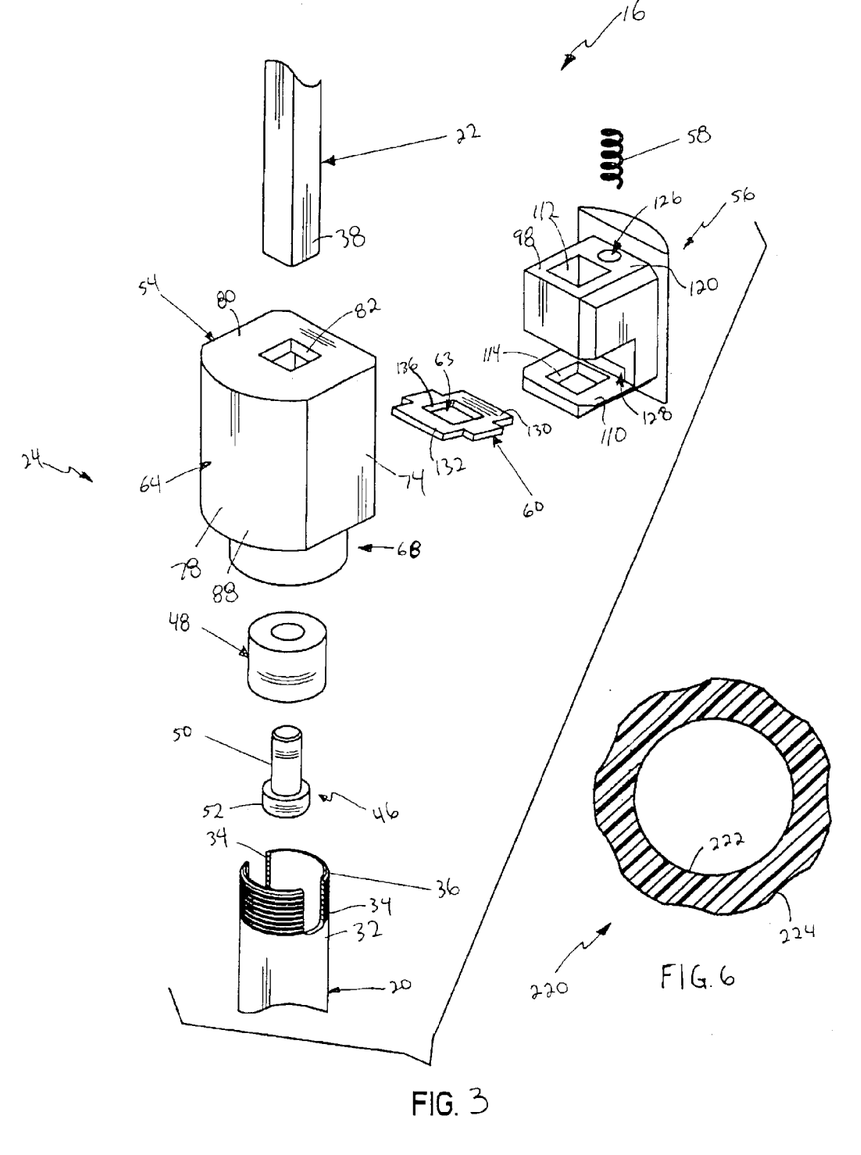
FIG. 3 is another exploded perspective view of the IV pole assembly of FIG. 1.
FIG. 6 is a cross-sectional view of an alternative embodiment base pole.

As shown in FIGS. 1–3, IV pole assembly 16 includes a base pole 20, an adjustment pole 22, and a coupling 24 configured to couple adjustment pole 22 to base pole 20 so that the overall length of IV pole assembly 16 can be adjusted by moving adjustment pole 22 relative to base pole 20 in directions 26, 28. According to the presently preferred embodiment of the disclosure, coupling 24 is configured to permit a user to lengthen IV pole assembly 16 by pulling up on adjustment pole 22, but will block a user from shortening IV pole assembly 16 unless coupling 24 is moved from a locked position to an unlocked position. Thus, the weight of adjustment pole 22 and the medical device supported thereon or any other force applied in first direction 26 will not cause the length of IV pole assembly 16 to decrease unless coupling 24 is moved to the unlocked position, but force applied in second direction 28 opposite to first direction 26 will cause the length of IV pole assembly 16 to increase regardless of whether coupling 24 is in the locked or unlocked position.

As shown in FIGS. 1–5, base pole 20 is preferably a cylindrical tube having a first end 30 coupled to bedframe 12 and formed to include a pair of notches 33 and a second end 32 formed to include a pair of notches 34 and serrations 36. Base pole 20 is preferably made of stainless steel. According to alternative embodiments of the present disclosure, other metals, plastics materials, composites, or other suitable materials known to those of ordinary skill in the art are used for the base pole.

According to an alternative embodiment of the present disclosure, a base pole 220, shown in FIG. 6, is provided that is made of a plastics material. Base pole 220 is preferably ultrasonically or otherwise welded to the coupling. As shown in FIG. 6, base pole 220 has a circular interior surface 222 and an undulate outer surface 224 that extends the length of base pole 220. Because base pole 220 is made of a plastics material, it can be submerged in an antiseptic bath for sterilization with the rest of the IV pole assembly without experiencing some of the corrosion problems associated with some metals.

As shown in FIGS. 1–5, adjustment pole 22 is preferably a square-shaped solid rod having a first end 38 formed to include female threads 40 and a second end 42 on which a plastic dual hook 44 or other medical device support is coupled. Adjustment pole 22 is preferably made of stainless steel. According to alternative embodiments of the present disclosure, other metals, plastics materials, composites, or other suitable materials known to those of ordinary skill in the art are used for the adjustment pole.

Figure 4:
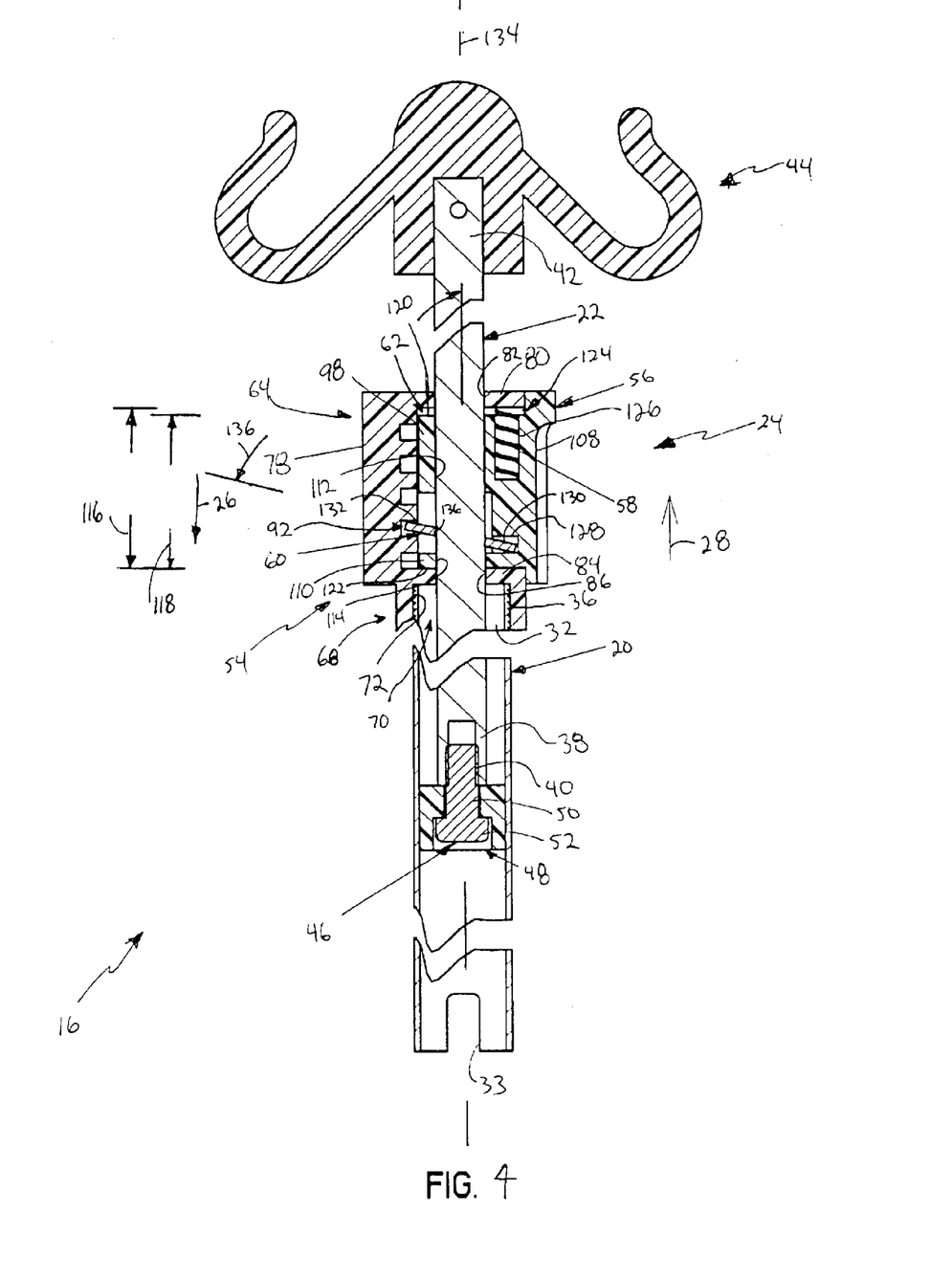
FIG. 4 is a cross-sectional view of the IV pole assembly of FIG. 1 showing the lock member in a locked position blocking the adjustment pole from moving relative to the base pole.

As shown in FIG. 2, IV pole assembly 16 further includes a stainless steel bolt 46 and a plastic insulative washer 48. Bolt 46 includes a shank 50 and a head 52 coupled to shank 50. Shank 50 is pushed through washer 48 and threaded into female threads 40 of adjustment pole 22 after adjustment pole 22 is fed through coupling 24 so that head 52 couples washer 48 to first end 38 of adjustment pole 22, as shown in FIG. 4. Washer 48 provides a spacer between first end 38 of adjustment pole 22 and base pole 20 to provide an electrical barrier therebetween.

Figure 5:
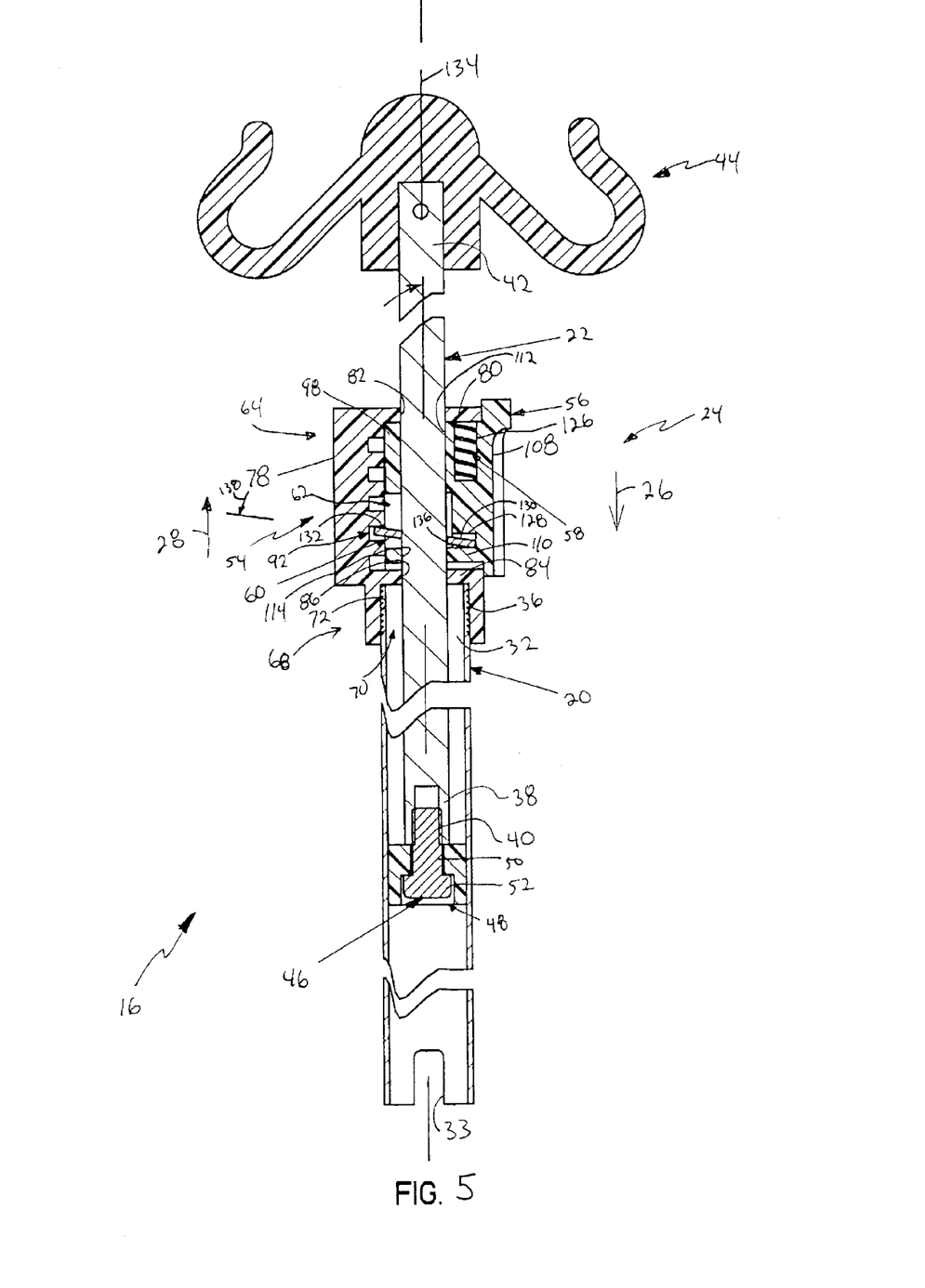
FIG. 5 is a cross-sectional view of the IV pole assembly of FIG. 1, similar to FIG. 4, showing the lock member in an unlocked position permitting movement of the adjustment pole relative to the base pole.

As seen in FIGS. 2 and 3, coupling 24 includes a box-shaped housing 54, a release 56, a stainless steel spring 58, and a plate-like lock member 60. Release 56, compression spring 58, and a plate-like lock member 60 are positioned within an interior region 62 of housing 54, as shown in FIGS. 4 and 5, and cooperate with housing 54 to block movement of adjustment pole 22 relative to base pole 20 depending on the direction of force applied to adjustment pole 22 and on whether coupling 24 is in the locked or unlocked position.

Lock member 60 is positioned on a portion of housing 54 and release 56 and includes a square aperture 63 sized to receive adjustment rod 22 therein. Spring 58 is positioned between release 56 and housing 54 to bias release 56 in first direction 26 to a locked position. When release 56 is in the locked position, lock member 60 binds adjustment rod 22 so that adjustment rod 22 is movable in second direction 28 to lengthen IV pole assembly 16, but not in first direction 26 to shorten IV pole assembly 16. As shown in FIG. 5, a user can move release 56 in direction 28 to an unlocked position against the bias of spring 58 so that adjustment rod 22 can be moved in first or second directions 26, 28 to shorten or length IV pole assembly 16.

Housing 54 is preferably a unitary member including a lock chamber section 64 defining an upper portion 66 of interior region 62 and a base section 68 defining a lower portion 70 of interior region 62. Base section 68 is cylindrical and includes an inner surface 72 which engages serrations 36 of base pole 20 to couple housing 54 to base pole 20. Base section 68 further includes a pair of lugs (not shown) on inner surface 72 sized to fit within notches 34 of base pole 20 to prevent housing 54 from rotating relative to base pole 20.

In addition to the insulative barrier provided by washer 48, base section 68 of housing 54 provides an electrical insulator between second end 32 of base pole 20 and adjustment rod 22. Thus, washer 48 and housing 54 cooperate to align adjustment rod 22 within base pole 20 so that adjustment rod 22 is electrically spaced apart from base pole 20.

As shown in FIG. 2, lock chamber section 64 has a pair of substantially flat sidewalls 74, 76, a back wall 78 extending between sidewalls 74, 76, a top wall 80 having a square aperture 82 formed therein, and a bottom wall 84 coupled to base section 68 and having another square aperture 86 formed therein. Sidewalls 74, 76, back wall 78, top wall 80, and bottom wall 84 cooperate to define an opening 94 into interior region 62. Back wall 78 has a curved outer surface 88 and a substantially vertical and flat inner surface 90 with a plurality of grooves 92 formed therein in which lock member 60 pivots. According to alternative embodiments of the present disclosure, only the second lowermost groove formed in the flat inner surface is provided.

As shown in FIGS. 4 and 5, release 56 is partially positioned within interior region 62 of housing 54. Release 56 includes an outer wall 96 that slides on edges 97 of sidewalls 74, 76 during movement between the locked and unlocked positions and a pair of spaced-apart pole guides 98, 110 coupled to outer wall 96 and extending into interior region 62. As shown in FIG. 2, outer wall 96 is formed to include a thumb-receiving recess 108 on which a user presses to move release 56 to the unlocked position. Each pole guide 98, 110 is formed to include a square aperture 112, 114 sized to receive adjustment pole 22 therein. Square apertures 112, 114 of release 56 and square apertures 82, 86 of housing 56 are sized to provide enough clearance between release 56 and housing 54 and adjustment rod 22 to permit adjustment rod 22 to move freely through housing 54 and release 56 without an undue amount of wobble. According to alternative embodiments of the present disclosure, the lower pole guide defines a pair of spaced apart tabs defining a notch therebetween configured to receive the adjustment pole.

Interior region 62 of housing 54 is sized to permit release 56 to move up and down adjustment rod 22 during movement between the locked and unlocked position as shown in FIGS. 4 and 5. Interior region 62 has a height 116 measured from top wall 80 to bottom wall 84. Height 116 is slightly larger than a distance 118 measured from a top surface 120 of upper pole guide 98 and a lower surface 122 of lower pole guide 110 so that a gap 124 exists between top wall 80 and upper pole guide 98 when release 56 is in the locked position as shown in FIG. 4. Gap 124 provides clearance between housing 54 and release 56 so that release 56 can slide to the unlocked position shown in FIG. 5.

Spring 58 is positioned between release 56 and top wall 80 of housing 54 with a portion of spring 58 positioned in gap 124 and a portion of spring 58 positioned in a spring-receiving bore 126 formed in upper pole guide 98. When IV pole assembly 16 is assembled, spring 58 is compressed to bias release 56 downwardly. Thus, after a user removes their thumb or other finger from thumb-receiving recess 108, spring 58 returns release 56 and lock member 60 to the locked position as shown in FIG. 4.

As shown in FIGS. 3–5, release 56 is formed to include a groove 128 sized to receive a first end 130 of lock member 60 therein. A second end 132 of lock member 60 is positioned in second lower most groove 92 formed in back wall 78 of housing 56 as shown in FIG. 4. When release 56 is in the locked position, second lower most groove 92 is slightly elevated relative to groove 128 of release 56 so that lock member 60 is titled/cocked relative to a longitudinal axis 134 of adjustment rod 22 in the locked position. When in the locked position, a plane of lock member 60 defines a first angle 136 relative to longitudinal axis 134 and an inner edge 136 of lock member 60 binds adjustment rod 22 to block movement of rod 22 in first direction 26, but permits movement of adjustment rod 22 in second direction 28.

When release member 56 is moved in direction 28 to the unlocked position, groove 128 and first end 130 of lock member 60 are raised in direction 28 while second end 132 of lock member 60 pivots in second lower most groove 92 of member 60 to the unlocked position as shown in FIG. 5. After movement to the unlocked position, the plane of lock member 60 defines a second angle 138 that is less than first angle 136. Because of this pivoting movement about a pilot axis, inner edge 136 of lock member 60 no longer binds adjustment rod 22 so that adjustment rod 22 can be moved in directions 26, 28 to shorten or lengthen the length of IV pole assembly 16.

Preferably, square apertures 82, 86, 112, 114, 63 of housing 54, release 56, and lock member 60 are of the same length and width so that an equal clearance is provided through which adjustment pole 22 may freely move. However, because the plane of lock member 60 is not perpendicular to longitudinal axis 134 of adjustment rod 22, the projected width of aperture 63 of lock member 60 along longitudinal axis 134 is less the width of the other square apertures 82, 86, 112, 114. Therefore, edge 136 binds adjustment rod 22 when the plane of lock member 60 deviates enough from being perpendicular to longitudinal axis 134 as shown in FIG. 4. As the plane of lock member 60 approaches nearer to perpendicular to longitudinal axis 134 when release 56 is raised, edge 136 provides less binding with adjustment rod 22 until the projected width of square aperture 63 is enough to permit adjustment rod 22 to slide in first direction 26. As shown in FIGS. 4 and 5, housing 54 and release 56 each provide a fulcrum or hinge point on which lock member 60 pivots when moved by release 56 between the locked and unlocked positions. Force applied to adjustment rod 22 in direction 28 causes a slight upward shifting of second end 130 of lock member 60 to increase the projected width of aperture 63 permitting adjustment pole 22 to move in direction 28 even when release 56 is in the locked position.

According to alternative embodiments, the position of grooves and/or size of the aperture formed in the lock member are changed so that the first and second angles defined by the lock member are different than those illustrated. For example, according to one alternative embodiment, the width of the aperture in the lock member is increased and the first end of the lock member is positioned in the third lowermost groove increasing the angle that the lock member deviates from perpendicular with the longitudinal axis.

For example, the width of the aperture in the lock member may be reduced requiring greater movement of the lock member (i.e., to a position at or near perpendicular to the longitudinal) to create enough clearance so that the adjustment pole can be moved relative to the base pole.

According to the preferred embodiments of the present disclosure, lock member 60 is made of corrosion resistive, heat-treated steel. According to other embodiments of the present disclosure, the lock member is made of stainless steel, other metals, plastics materials, composites, or any other-suitable material known to those of ordinary skill in the art. According to other embodiments of the present disclosure, the lock member is coated with a material to provide the lock member with a desired coefficient of friction for binding the adjustment pole. According to other alternative embodiments of the present disclosure, the lock member is a laminate having multiple edges defining an aperture for receiving and binding the adjustment rod. According to other alternative embodiments of the present disclosure, the lock member is substantially round, substantially square, or any other suitable shape known to those of ordinary skill in the art.

To assemble IV pole assembly 16, first end 130 of lock member 60 is positioned in groove 128 of release 56 and spring 58 is positioned in spring-receiving bore 126. Spring 58 is then compressed to substantially fit within spring-receiving bore 126. While spring 58 is compressed, upper and lower pole guides 98, 110 and lock member 60 are positioned in interior region 62 of housing 64 so that second end 132 of lock member 60 is positioned in second lower most groove 92 formed in back wall 78 of housing 54.

After release 56 and lock member 60 are inserted into interior region 62, square apertures 82, 86, 112, 114, 63 of housing 54, release 56 and lock member 60 are substantially aligned. Adjustment rod 22 is then fed through these apertures 82, 86, 112, 114, 63 so that first end 38 of adjustment rod 22 through coupling 24 extends beyond base portion 68 of housing 54.

Once adjustment rod 22 is inserted through coupling 24, washer 48 is coupled to first end 38 of adjustment rod 22 by bolt 46 as previously mentioned. Washer 48, bolt 46, and first end 38 of adjustment rod 22 are then positioned within base pole 20 and coupling 24 is forced on second end 32 of base pole 20 so that serrations 36 grip inner surface 72 of base portion 68 of housing 54 with the lugs of base portions 68 positioned in notches 34. Because washer 48 is larger than aperture 86 of bottom wall 84 of housing 54, adjustment rod 22 is blocked from being pulled through coupling 24. Furthermore, after adjustment rod 22 is inserted through coupling 24, release 56 and lock member 60 are blocked from being withdrawn from interior region 62 of housing 54 by adjustment rod 22.

To disassemble IV pole assembly 16, washer 48 is removed from first end 38 of adjustment pole 22 through first end 30 of base pole 20. Then, adjustment pole 22 is removed from within coupling 24 so that release 56, lock member 60, and spring 58 can be removed from within interior region 62 of housing 54.

IV pole assembly 16 is configured to resist corrosion caused by cleaning. For example, base pole 20, adjustment pole 22, spring 58, and bolt 46 are made of stainless steel; hook 44, housing 54, release 56, and washer 48 are made of plastics material; and lock member 60 is made of corrosion resistive steel. All of these material are resistant to corrosion caused by water and standard hospital cleaning agents used to clean and disinfect the components of IV pole assembly 16. Thus, all of IV pole assembly 16 may be submerged in an antiseptic bath or otherwise cleaned with solutions that would otherwise cause standard steel and other common materials to rust or otherwise corrode. According to the present disclosure, other corrosion-resistant material, such as aluminum, plastics materials, coated metals, are used for the various components of the IV pole assembly.

Although the invention has been described in detail with reference to preferred embodiments, variations and modifications exist within the scope and spirit of the invention as described and defined in the following claims.

What is claimed is:

1. A medical device support apparatus comprising
   a telescoping pole assembly including a first member and a second member movable relative to the first member along an axis in a first direction and a second direction opposite to the first direction,
   a lock member formed to include an edge defining a four-sided aperture, the second member being received in the aperture, the lock member having a second position in which the edge engages the second member to prevent movement of the second member relative to the first member in the first direction and the lock member having a first position in which the edge disengages from the second member so that the second member is movable along the axis relative to the first member in the first direction and the second direction,
   a housing, and
   a release configured to move the lock member between the first and second positions, the release being positioned to slide on an external surface of the housing during movement of the lock member between the first and second positions.

2. The medical device support of claim 1, wherein the lock member and the axis define a first angle therebetween when the lock member is in the first position and a second angle that deviates from the first angle when the lock member is in the second position.

3. The medical device support of claim 1, wherein the housing is coupled to the telescoping pole assembly and the lock member is positioned in an interior region of the housing.

4. The medical device support of claim 3, wherein the lock member is pivotably coupled to the housing.

5. The medical device support of claim 1, wherein the edge is continuous.

6. The medical device support of claim 1, wherein the lock member is plate-like.

7. The medical device support of claim 1, wherein the lock member, when in the second position, allows movement of the second member relative to the first member in the second direction.

8. The medical device support of claim 7, wherein the lock member and the axis define a first angle therebetween when the lock member is in the first position and a second angle that deviates from the first angle when the lock member is in the second position.

9. The medical device support of claim 7, wherein the lock member is pivotably coupled to the housing.

10. The medical device support of claim 7, wherein the edge is continuous.

11. The medical device support of claim 7, wherein the lock member is plate-like.

* * * * *